United States Patent [19]

Post

[11] Patent Number: 5,683,423
[45] Date of Patent: Nov. 4, 1997

[54] DEFIBRILLATOR AND METHOD FOR STORING SELECTED SEGMENTS OF AUDIO DATA

[75] Inventor: William Lewis Post, McMinnville, Oreg.

[73] Assignee: Hewlett-Packard Company, Palo Alto, Calif.

[21] Appl. No.: 615,911

[22] Filed: Mar. 14, 1996

[51] Int. Cl.$^6$ ................................. A61N 1/39
[52] U.S. Cl. .................. 607/5; 128/709; 128/710
[58] Field of Search .............. 607/5, 4; 128/709, 128/710

[56] References Cited

U.S. PATENT DOCUMENTS

| | | | |
|---|---|---|---|
| 4,223,678 | 9/1980 | Langer et al. | 607/5 |
| 4,610,254 | 9/1986 | Morgan et al. | 607/6 |
| 4,667,682 | 5/1987 | Ihlenfeld, III | 128/711 |
| 5,027,824 | 7/1991 | Dougherty et al. | 128/710 |
| 5,097,830 | 3/1992 | Eikefjord et al. | 607/5 |
| 5,405,362 | 4/1995 | Kramer et al. | 607/5 |

Primary Examiner—William E. Kamm
Assistant Examiner—Kennedy J. Schaetzle

[57] ABSTRACT

A defibrillator and method for storing selected audio data during treatment of a patient are disclosed. The defibrillator includes a charge storage unit for storing an electrical charge and a discharge apparatus coupled to the charge storage unit for delivering the electrical charge to a patient. In addition, a sensor is provided for sensing electrocardiogram (ECG) data of the patient. The defibrillator further includes a memory and a data processor coupled both to the sensor and to the memory. The data processor stores ECG data sensed from the patient within the memory. The defibrillator also has an audio recorder, wherein the audio recorder detects and records audio data for a selected time period in response to detection of a selected event such that audio data is recorded only for selected time periods during the operation of the defibrillator. In a preferred embodiment of the present invention, the defibrillator also includes an input device coupled to the data processor. In this embodiment, the audio recorder stores audio data for a selected time period in response to a manipulation of the input device.

20 Claims, 2 Drawing Sheets

DEFIBRILLATOR AND METHOD FOR STORING SELECTED SEGMENTS OF AUDIO DATA

BACKGROUND OF THE INVENTION

1. Technical Field

The present invention relates in general to a cardiac defibrillator and in particular to a cardiac defibrillator which includes voice recording facilities. Still more particularly, the present invention relates to a cardiac defibrillator and method which record audio data for selected time periods during the provision of emergency medical care.

2. Description of the Related Art

The hearts of persons requiring medical care, for example, persons suffering from severe trauma or a heart attack, occasionally lapse into an irregular rhythm of rapid arrhythmias, known as fibrillation, flutter, and tachycardia. These irregular heart rhythms require prompt management with antiarrhythmic drugs and/or localized electrical stimulation. A defibrillator is a medical device utilized to apply an electric shock to a patient's heart, thereby restoring the heart to a normal sinus rhythm. In general, medical instrumentation manufacturers have developed two types of defibrillators—prehospital defibrillators, which are typically battery powered, portable products utilized by Emergency Medical Service (EMS) personnel prior to admittance of the patient to a hospital, and hospital defibrillators, which as the name implies, are utilized during hospital treatment of arrhythmic patients.

In order to permit EMS personnel to record information concerning the status and treatment of a patient requiring defibrillation for possible subsequent use by hospital medical personnel, conventional prehospital defibrillators are often equipped with facilities for recording audio data. These conventional prehospital defibrillators typically record audio data for the duration of time that the defibrillator is powered on. Thus, in addition to important information, such as the patient's name or description, the type and amount of drugs administered, the number of shocks delivered, and the patient's condition, conventional prehospital defibrillators record 20–30 minutes of extraneous audio data that is irrelevant to the treatment of the patient. Because such audio data recordings typically comprise a large body of unnecessary data interspersed with brief segments of important information, the audio data recordings are seldom reviewed by hospital medical personnel and are therefore of little use. In addition, because of the large volume of data that is recorded, conventional prehospital defibrillators require an audio tape recorder or multiple megabyte digital memory to store the audio data recording, consequently raising the cost of the defibrillator significantly.

Thus, as should be apparent, it would be desirable to provide an improved defibrillator and method for recording audio data during the defibrillation of an arrhythmic patient which record only pertinent information concerning the treatment and condition of the patient.

SUMMARY OF THE INVENTION

It is therefore one object of the present invention to provide an improved cardiac defibrillator.

It is another object of the present invention to provide an improved cardiac defibrillator which includes voice recording facilities.

It is yet another object of the present invention to provide an improved cardiac defibrillator and method which record audio data for selected time periods during the provision of emergency medical care.

The foregoing objects are achieved as is now described. A defibrillator and method for storing selected audio data during treatment of a patient are disclosed. The defibrillator includes a charge storage unit for storing an electrical charge and a discharge apparatus coupled to the charge storage unit for delivering the electrical charge to a patient. In addition, a sensor is provided for sensing electrocardiogram (ECG) data of the patient. The defibrillator further includes a memory and a data processor coupled both to the sensor and to the memory. The data processor stores ECG data sensed from the patient within the memory. The defibrillator also has an audio recorder, wherein the audio recorder detects and records audio data for a selected time period in response to detection of a selected event such that audio data is recorded only for selected time periods during the operation of the defibrillator. In a preferred embodiment of the present invention, the defibrillator also includes an input device coupled to the data processor, In this embodiment, the audio recorder stores audio data for a selected time period in response to a manipulation of the input device.

The above as well as additional objects, features, and advantages of the present invention will become apparent in the following detailed written description.

BRIEF DESCRIPTION OF THE DRAWINGS

The novel features believed characteristic of the invention are set forth in the appended claims. The invention itself however, as well as a preferred mode of use, further objects and advantages thereof, will best be understood by reference to the following detailed description of an illustrative embodiment when read in conjunction with the accompanying drawings, wherein:

DETAILED DESCRIPTION OF PREFERRED EMBODIMENT

Figure 1:
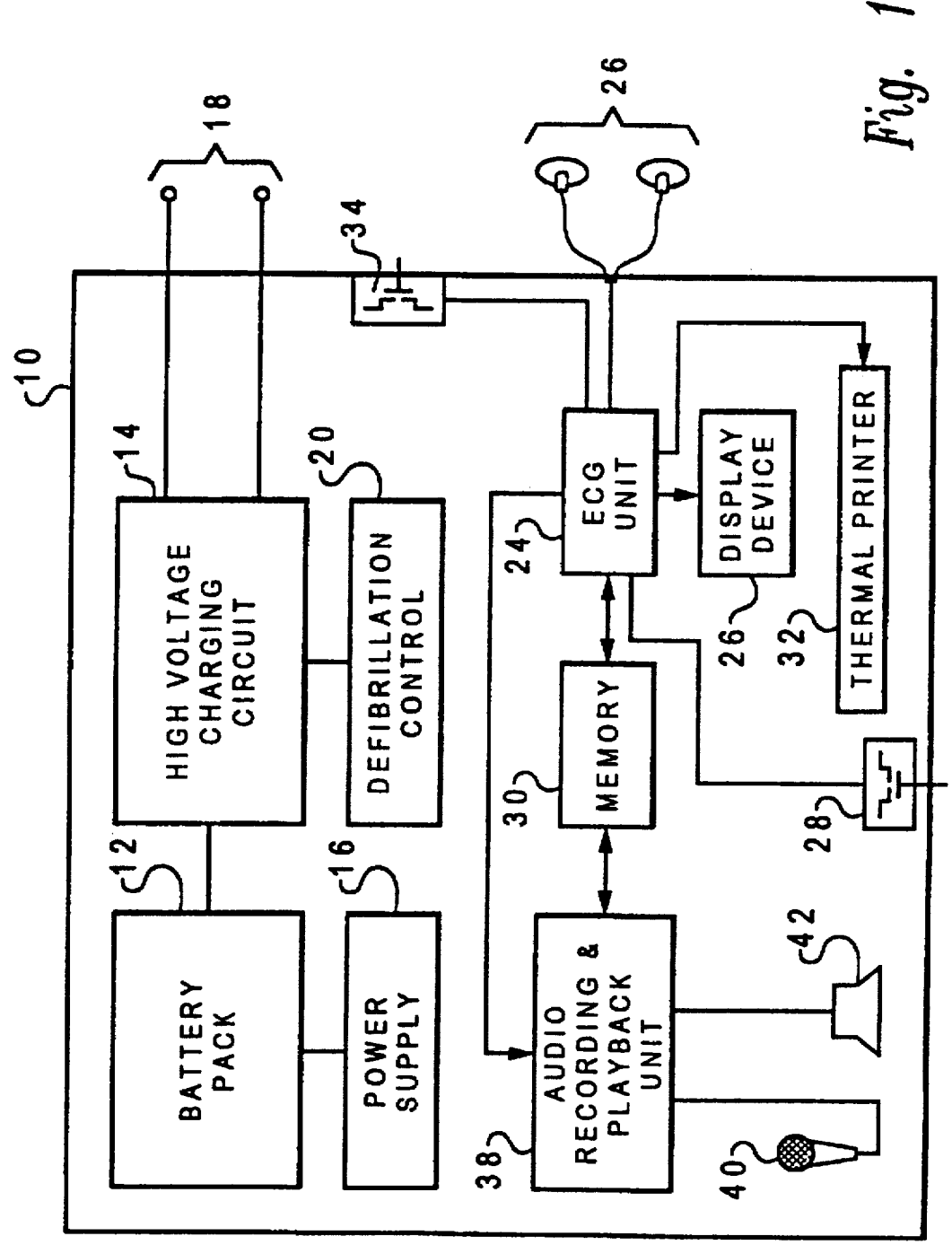
FIG. 1 illustrates a block diagram of a preferred embodiment of a defibrillator in accordance with the present invention.

With reference now to the figures and in particular with reference to FIG. 1, there is illustrated a block diagram of a defibrillator in accordance with the present invention. Defibrillator 10 includes a rechargeable battery pack 12, which supplies power to defibrillator 10. As a battery-powered device, defibrillator 10 is highly portable and therefore suitable for pre-hospital (emergency) use. Battery pack 12 preferably includes one or more nickel-cadmium (NiCd) batteries capable of providing power for several hours of operation. As illustrated, battery pack 12 is electrically coupled to high voltage charging circuit 14 and supplies charge to a large capacitor contained within high voltage charging circuit 14 utilized to store the large charge required to defibrillate an arrhythmic patient. Battery pack 12 is further electrically coupled to power supply 16, which supplies power to the control and monitoring circuitry within defibrillator 10. High voltage charging circuit 14 is electrically connected to a pair of paddles 18 utilized to deliver a defibrillating shock to an arrhythmic patient. The delivery of the defibrillating shock to the arrhythmic patient by a high voltage charging circuit 14 is controlled by defibrillation control 20.

Still referring to FIG. 1, defibrillator 10 further includes electrocardiogram (ECG) unit 24, which controls the monitoring functions of defibrillator 10. From the following description of ECG unit 24, those skilled in the art will appreciate that ECG unit 24 may be implemented utilizing a conventional microprocessor and support circuitry, or alternatively, a application-specific integrated circuit (ASIC). ECG unit 24 receives ECG data from a patient through chest electrodes 26, which are preferably coated with a conductive gel to establish a good electrical contact with the patient. The ECG data received from the patient is temporarily buffered in an ECG data buffer within ECG unit 24 and displayed in real-time to the operator of defibrillator 10 within display device 26. The ECG data is preferably displayed in the form of a conventional ECG waveform trace, and may be displayed in conjunction with additional information extracted from the ECG data, such as the patient's instantaneous pulse rate.

ECG unit 24 is further coupled to "mark" button 28, which is depressed by an operator to store ECG data of interest within memory 30. In response to the operator depressing mark button 28, ECG unit 24 stores a short duration (e.g., 15 seconds) of ECG data preceding the depression of mark button 28 and a short duration of ECG data following the depression of mark button 28 from the ECG data buffer to memory 30. Accordingly, the ECG data buffer within ECG unit 24 is preferably designed to store at least the amount of ECG data sensed within the longest ECG segment that the operator may desire to store within memory 30. During treatment of a patient, the operator typically utilizes mark button 28 to record, segments of ECG data sensed before and after the administration of drugs, the delivery of shocks, and other major treatment events. The collection of ECG data segments stored within memory 30 by the operator during treatment of a patient, known as a "code" summary, can be printed by the operator of defibrillator 10 on thermal printer 32 by depressing review button 34.

In addition to recording ECG data in response to a user's depression of mark button 28 as described above, ECG unit 24 preferably supports one or more automated modes of storing ECG data. For example, ECG unit 24 could store all of the patient's ECG data sensed during treatment within memory 30 in conjunction with a list of marked events for later use. Alternatively, ECG unit could automatically mark events preselected by the operator, such as the delivery of shocks.

ECG unit 24 is further coupled to audio recording and playback unit 38 by control signals 36. Audio recording and playback unit 38 receives audio input from microphone 40 and presents audio output to the operator of defibrillator 10 through speaker 42. In accordance with the present invention, when mark button 28 is depressed by the operator, ECG unit 24 asserts one or more of control signals 36 for a selected period of time, for example, 15 seconds. In response to the assertion of control signals 36 indicating that mark button 28 has been depressed, audio recording and playback unit 38 senses audio data via microphone 40, digitizes the audio data, and stores the audio data within memory 30. As will be appreciated by those skilled in the art, the audio data can be compressed prior to storage utilizing any of a number of well-known data compression algorithms in order to minimize the amount of memory 30 required to store the audio data. In a preferred embodiment of the present invention, the audio data recorded in response to depression of mark button 28 is stored within memory 30 in association with the ECG data recorded in response to the same depression of mark button 28. In an alternative embodiment of the present invention, the audio data is stored by audio recording and playback unit 38 on magnetic tape, such as audio cassette or microcassette tape. Recording audio data for only selected time periods during the operation of defibrillator 10 enables the operator to make a voice recording of important information such as patient name and description, amounts and types of drugs administered, the number of shocks delivered, and other events of interest, without including extraneous audio data. Like the storage of ECG data, the storage of audio data can be automated under the control of ECG unit 24. For example, defibrillator 10 can automatically record audio data in response to the delivery of shocks, turning on electrodes 26, or other events of interest.

According to a preferred embodiment of the present invention, when the operator depresses review button 34, ECG unit 24 asserts selected control signals 36 to cause audio recording and playback unit 38 to retrieve each stored segment of audio data from memory 30 and playback the recorded audio data to the operator through speaker 42. Thus, the operator of defibrillator 10 can easily and quickly review important audio information stored within memory 30 while reviewing the code summary. To facilitate the transportability of audio and ECG data stored within memory 30, memory 30 preferably comprises a removable and portable data storage device, such as a PCMCIA (Personal Computer Memory Card International Association) memory card; however, memory 30 can alternatively be implemented as a nonremovable memory. In addition, defibrillator 10 preferably includes an infrared serial port or other data communication means (not illustrated) to enable the contents of memory 30 to be directly downloaded to a computer for review and analysis.

Figure 2:
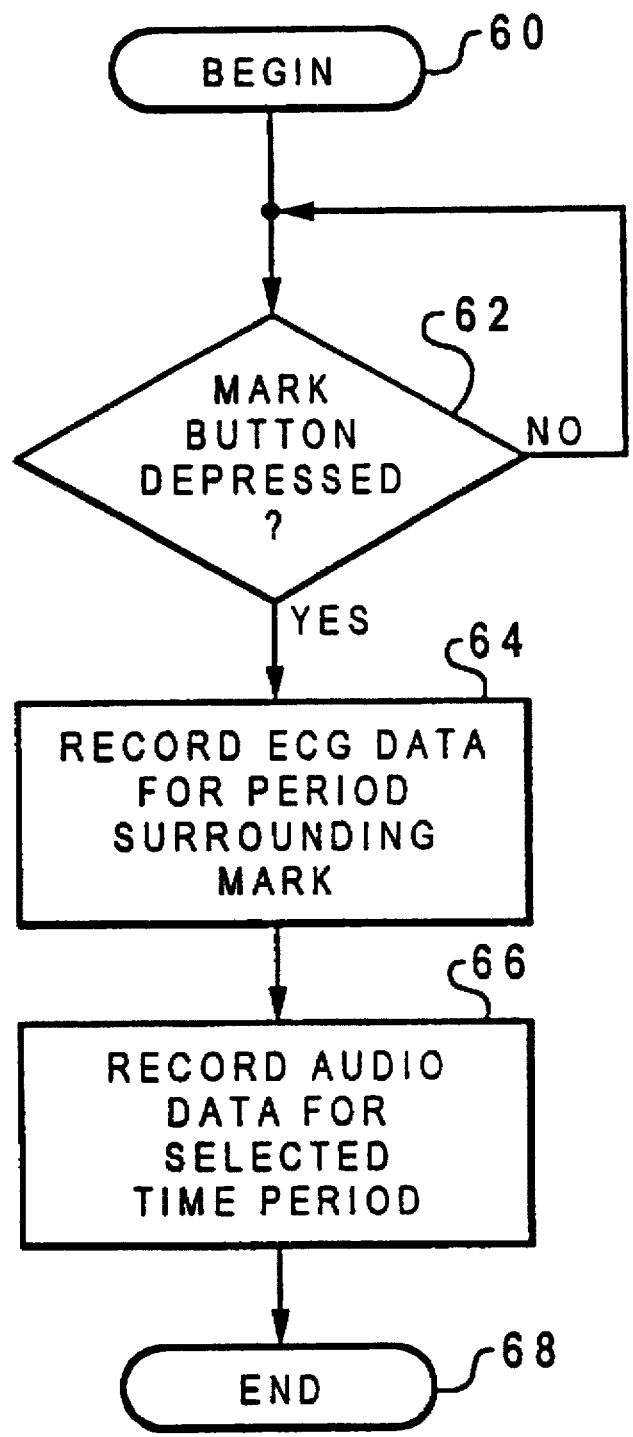
FIG. 2 is a flowchart depicting a method for recording audio data within a defibrillator for a selected time period in accordance with the present invention.

Referring now to FIG. 2, there is depicted a flowchart of a preferred embodiment of a method of recording audio data within a defibrillator in accordance the present invention. As illustrated, the process begins at block 60 when defibrillator 10 is powered on by the operator. In contrast to many conventional defibrillators equipped with voice recording facilities, defibrillator 10 does not begin recording audio data immediately following the operator powering on defibrillator 10. Instead, the process proceeds from block 60 to block 62, which illustrates a determination of whether or not mark button 28 has been depressed or whether an event that triggers an automatic mark has occurred. If not, the process simply iterates at block 62 until such time as mark button 28 is depressed or an event that automatically triggers a mark occurs.

In response to the depression of mark button 28 by the operator or the occurrence of an automatic mark event, the process proceeds from block 62 to block 64, which depicts ECG unit 24 storing ECG data for a selected time period surrounding the depression of mark button 28 (or the automatic mark event) within memory 30. In addition, as depicted within block 66, ECG unit 24 causes audio recording and playback unit 38 to record a selected duration of audio data within memory 30. As described above, the segment of audio data stored within memory 30 is preferably stored in association with the ECG data stored in response to the same depression of mark button 28 in order to easily facilitate the playback of audio data segments when the corresponding ECG data in the code summary is reviewed. Thereafter, the process passes to block 68 and returns.

As has been described, the present invention provides an improved defibrillator and a method for storing selected segments of audio data during the operation of the defibrillator. Because a defibrillator in accordance with the present invention stores only selected segments of audio data rather than audio data recorded continuously during the operation of the defibrillator, the present invention enables the memory which stores the audio data to be greatly reduced in size. In addition, the present invention facilitates the review of audio data recorded during operation of the defibrillator.

While the invention has been particularly shown and described with reference to a preferred embodiment, it will be understood by those skilled in the art that various changes in form and detail may be made therein without departing from the spirit and scope of the invention.

What is claimed is:

1. A defibrillator, comprising:

a charge storage device that stores an electrical charge;

discharge means coupled to said charge storage device for delivering said electrical charge to a patient;

a sensor that senses electrocardiogram (ECG) data of said patient;

a memory;

a data processor coupled to said sensor and to said memory, said data processor including means for storing ECG data within said memory;

a power supply having a power on state; and an audio recorder coupled to said power supply, wherein when said power supply is in said power on state said audio recorder receives electrical power from said power supply and detects and records audio data for a plurality of noncontiguous time periods in response to detection of a corresponding plurality of selected events.

2. The defibrillator of claim 1, and further comprising:

an operator input device coupled to said data processor, wherein in response to operator manipulation of said operator input device, said means for storing ECG data stores, within said memory, ECG data sensed during a particular time period.

3. The defibrillator of claim 2, wherein said audio recorder detects and records audio data for one of said plurality of noncontiguous time periods in response to operator manipulation of said operator input device.

4. The defibrillator of claim 1, wherein said audio recorder stores said audio data within said memory.

5. The defibrillator of claim 4, wherein said audio recorder stores said audio data in association with ECG data sensed during a same one of said plurality of noncontiguous time periods.

6. The defibrillator of claim 4, wherein said audio recorder includes means for compressing said audio data prior to storage of said audio data within said memory.

7. The defibrillator of claim 1, wherein said audio recorder comprises a magnetic tape storage device.

8. The defibrillator of claim 1, wherein said audio recorder detects and records audio data for one of said plurality of noncontiguous time periods in response to detection of ECG data defining one of said plurality of selected events.

9. A method for recording audio data within a defibrillator during treatment of a patient, said defibrillator including an audio recorder and a sensor for sensing electrocardiogram (ECG) data of said patient, said method comprising:

supplying power to said defibrillator;

sensing electrocardiogram (ECG) data of said patient utilizing said sensor;

storing said ECG data of said patient; and recording audio data for a plurality of noncontiguous time periods in response to detection of a corresponding plurality of selected events occurring while power is supplied to said defibrillator.

10. The method for recording audio data of claim 9, said defibrillator further including an operator input device, wherein said step of storing said ECG data of said patient is performed in response to operator manipulation of said operator input device.

11. The method for recording audio data of claim 10, wherein said selected event comprises a manipulation of said operator input device.

12. The method for recording audio data of claim 9, said defibrillator further including a memory, wherein said step of recording audio data comprises storing said audio data within said memory.

13. The method for recording audio data of claim 12, wherein said audio data is stored in association with ECG data sensed during a same one of said plurality of noncontiguous time periods.

14. The method for recording audio data of claim 12, wherein said step of storing said audio data further comprises compressing said audio data prior to storage of said audio data.

15. The method for recording audio data of claim 9, wherein said one of said plurality of selected events is defined by selected ECG data.

16. A medical device, said medical device comprising:

a sensor that senses data concerning a condition of a patient;

a memory;

a data processor coupled to said sensor and coupled to said memory, said data processor including means for storing said data within said memory;

a power supply having a power on state; and an audio recorder coupled to said power supply, wherein when said power supply is in said power on state said audio recorder receives electrical power from said power supply and detects and records audio data for a plurality of noncontiguous time periods in response to detection of a corresponding plurality of selected events.

17. The medical device of claim 16, wherein said medical device further comprises:

a charge storage device that stores an electrical charge; and discharge means coupled to said charge storage device for delivering said electrical charge to said patient.

18. The medical device of claim 16, and further comprising:

an operator input device coupled to said data processor, wherein in response to operator manipulation of said operator input device, said means for storing data stores data within said memory that was sensed during a particular time period.

19. The medical device of claim 18, wherein said audio recorder detects and records audio data for one of said plurality of noncontiguous time periods in response to operator manipulation of said operator input device.

20. The medical device of claim 16, wherein said audio recorder detects and records audio data for one of said plurality of noncontiguous time periods in response to detection of data defining one of said plurality of selected events.

* * * * *